(12) United States Patent
Burghart et al.

(10) Patent No.: US 8,293,272 B2
(45) Date of Patent: Oct. 23, 2012

(54) SOLID PHARMACEUTICAL PREPARATION CONTAINING LEVOTHYROXINE AND/OR LIOTHYRONINE SALTS

(75) Inventors: Walter Burghart, Vienna (AT); Kurt Burghart, Wiener Neustadt (AT); Johannes Raneburger, Wörgl (AT)

(73) Assignee: Globopharm Pharmazeutische Produktions-und Handelsgesellschaft m.b.H., Wiener Neustadt (AT)

( * ) Notice: Subject to any disclaimer, the term of this patent is extended or adjusted under 35 U.S.C. 154(b) by 844 days.

(21) Appl. No.: 10/555,354

(22) PCT Filed: May 3, 2004

(86) PCT No.: PCT/AT2004/000150
§ 371 (c)(1), (2), (4) Date: Nov. 2, 2005

(87) PCT Pub. No.: WO2004/096177
PCT Pub. Date: Nov. 11, 2004

(65) Prior Publication Data
US 2007/0014851 A1    Jan. 18, 2007

(30) Foreign Application Priority Data
May 2, 2003    (AT) .................................. A 667/2003

(51) Int. Cl.
*A61K 9/20*    (2006.01)

(52) U.S. Cl. ....................................................... 424/464
(58) Field of Classification Search ........................ None
See application file for complete search history.

(56) References Cited

U.S. PATENT DOCUMENTS

| | | | |
|---|---|---|---|
| 5,225,204 A | 7/1993 | Chen et al. | |
| 5,322,161 A * | 6/1994 | Shichman et al. | 206/204 |
| 5,324,522 A * | 6/1994 | Krenning et al. | 424/456 |
| 5,635,209 A | 6/1997 | Groenewoud et al. | |
| 5,955,105 A | 9/1999 | Mitra et al. | |
| 5,958,979 A | 9/1999 | Lahr et al. | |
| 6,399,101 B1 * | 6/2002 | Frontanes et al. | 424/488 |
| 2003/0099698 A1 * | 5/2003 | Hanshew et al. | 424/465 |
| 2003/0180353 A1 * | 9/2003 | Franz et al. | 424/465 |

FOREIGN PATENT DOCUMENTS

| | | |
|---|---|---|
| JP | 2002-284679 | 10/2002 |
| WO | WO 99/25343 A1 * | 5/1999 |

OTHER PUBLICATIONS

Fontana, Jr., Anthony; "Pharmaceutical Applications for Water Activity", Pharmaceutical Online article dated Apr. 29, 1999.*
Heidemann et al., Pharmaceutical Research, 8(3), p. 292-297, 1991.*

* cited by examiner

*Primary Examiner* — Nissa Westerberg
(74) *Attorney, Agent, or Firm* — Jacobson Holman PLLC

(57) ABSTRACT

In a solid pharmaceutical preparation containing water-soluble salts of levothyroxine and/or liothyronine as active ingredients, the water activity of said pharmaceutical preparation is adjusted to values of below 0.4 and, preferably, 0.1 to 0.3, measured at room temperature.

10 Claims, No Drawings

SOLID PHARMACEUTICAL PREPARATION CONTAINING LEVOTHYROXINE AND/OR LIOTHYRONINE SALTS

The invention relates to a solid pharmaceutical preparation containing water-soluble salts of levothyroxine and/or liothyronine as active ingredients.

Thyroid hormones of the initially defined kind have been available on the market in different packagings. Conventional thyroid hormone tablets require a number or measures to ensure that the active ingredient will be homogenously distributed among all the tablets of a batch and present in the same active ingredient concentration over time. Such problems in regard to what is called "content uniformity" also involve a number of problems relating to the stability of the active ingredient. Thus, it is, for instance, known that levothyroxine sodium salts and liothyronine sodium salts, if present as potassium salts, are water-insoluble and, hence, no longer available to the organism in an effective form. Furthermore, an instability and, in particular, storage instability were found as a function of moisture, temperature and light. As a result, numerous attempts have been made to enhance the stability of thyroid hormone tablets, wherein it has so far been basically attempted to enhance said stability by the addition of auxiliary agents positively influencing the same. To this end, U.S. Pat. No. 5,225,204 proposed to use water-soluble polyvinylpyrrolidone in addition to the respective sodium salts and adsorb the resulting mixture on a cellulose carrier to form a tablet, powder or capsule.

In U.S. Pat. No. 5,635,209, also sodium iodide as well as a wetting agent and a lubricant are used in addition to the sodium salt of levothyroxine-Na.

In U.S. Pat. No. 5,958,979, sodium thiosulfate is proposed as a stabilizing component.

From U.S. Pat. No. 6,399,101 it can be taken that the use of siliconized microcrystalline cellulose is to be of advantage.

All those known attempts do provide some stability improvement still do not safeguard sufficient stability over the required storage time, wherein it is, in particular, not readily feasible to guarantee homogeneity, which is difficult to maintain taking into account the relatively low dosage of thyroid hormones.

Levothyroxine-Na, as a rule, is present in the form of a pentahydrate that is stable at room temperature. Such a pentahydrate has a measured water activity of about 0.4 to 0.6 at room temperature. In this respect, by water activity the equilibrium moisture content is to be understood, 50% relative moisture corresponding to a water activity of 0.5 at a defined temperature.

The invention now aims to ensure, in a manner largely independent of the addition of auxiliary agents and, in particular, without any addition of specific, supposedly stability-enhancing adjuvants, an enhanced stability of said pharmaceutical preparation, a rapid and simple producibility of the same, an enhanced homogeneity of distribution of the active ingredient as well as a rapid dissolution of the active ingredient (optimum bioavailability). To solve this object, the solid pharmaceutical preparation according to the invention essentially consists in that the water activity of said pharmaceutical preparation is adjusted to values of below 0.4 and, preferably, 0.1 to 0.3, measured at room temperature. It has, in fact, turned out in a surprising manner that the stability will be substantially enhanced, if at least one mol of water is extracted from the active ingredient, which is usually present in pentahydrate form, wherein it merely has to be taken care that, when choosing auxiliary agents to be optionally used, the use of hygroscopic adjuvants is to be avoided in order to prevent water from being taken up again. This surprising effect is supposed to be due to the fact that in the usually present pentahydrate one mol of water, as opposed to the remaining four mols of water, is not present as a classic hydrate but in cluster form. It is exactly that water exceeding four mols of water, which can readily escape into the gas phase, yet again be reinserted into the cluster form of the levothyroxine crystals in an equally easy manner. This mol of water present in cluster form is, thus, relatively easily movable and only loosely bound to the crystal, which is also reflected by an accordingly elevated water activity at room temperature. While the active ingredient is sufficiently stable per se despite that fifth, relatively easily movable mol of water, this volatile and easily movable water not bound within the crystal, along with the usual adjuvants necessary for the production of tablets, will cause that mol of cluster water to induce an interaction with, and, in particular, dissolution of, adjuvant portions and said dissolved adjuvant portions, in combination with the free cluster water, to affect the stability of levothyroxine-Na to an extent no longer acceptable. Liothyronine-Na likewise contains up to 4% water, exhibiting the same stability behavior as levothyroxine-Na. It has now been demonstrated in a surprising manner that an appropriate long-term storage stability will be guaranteed, if this relatively easily movable water is eliminated by lowering the water activity at room temperature to values of below 0.4 and, in particular, 0.1 to 0.3, even without any specific stabilizing adjuvants. By uncontrolled drying and lowering of the water activity to below 0.1, levothyroxine-Na will pass into an amorphous state, thus becoming more and more instable again. This will, in turn, cause the solubility behavior to change in the negative sense towards poorer dissolution. The optimum water activities indicated will be achieved either by an accordingly dry processing in tablet production, using accordingly dry starting substances at controlled water activities with the active ingredient too being admixed in an accordingly dried form (water activity) and directly tableted after this, or by the drying of the tablet mixture to the required water activity, or by the selective after-drying of the ready-made tablets. The production of tablets having such low water activities, in practice, is not readily feasible—great attention having to be paid to the homogenous application of the active ingredient on a carrier having as large a surface area as possible. The addition of appropriate amounts of a tablet wetting agent allows for fine-tuning to low water activities in the order of 0.1. If such a tablet, which may have a water activity of, for instance, 0.1 to 0.3, is subsequently tightly packed too, sufficient stability and storability will be ensured. Besides the option of providing an accordingly tight package, the optimum water activity will also be attained in that largely or exclusively non-hygroscopic adjuvants which are known for low water activities at room temperature, such as, for instance, mannitol or the like, are used for the production of such tablets and the tablets are subsequently packed in usual blister packages.

The problem of a rapid active ingredient dissolution an, hence, rapid and full bioavailability, which is not always guaranteed in known compositions, will be solved in a particularly simple manner in that the active ingredient is homogenously applied on a water-soluble carrier. Such a water-soluble carrier, after the administration of the tablet, will consequently cause the active ingredient to dissolve rapidly and reliably without requiring the use of a wetting agent, since the poorly water-soluble active ingredient applied on the water-soluble carrier in a finely distributed manner will rapidly dissolve along with the water-soluble carrier. In an advantageous manner, mannitol is used as a water-soluble carrier.

In order to counter the problem of an activity decrease due to the formation of water-insoluble salts, it is advantageous to take into account the respective calcium content in the carrier materials, adjuvatns or solvents employed. In this respect, the configuration is advantageously devised such that the carrier is treated with an amount of EDTA-Na substantially corresponding to the $Ca^{++}$-content of the carrier and, optionally, with an additional admixture of citric acid, in order to safeguard that unavoidable $Ca^{++}$-ions as occur particularly in water-soluble carriers will not create any disturbing effect. Treatment is effected from an aqueous solution while taking care that water will be eliminated until the predetermined water activity has been reached. In the main, the desired homogeneity, the desired solubility and, in particular, the solubility under formation of a clear solution, the rapid producibility and the elevated stability due to anhydrous operation will be guaranteed in that the preparation is present in the form of tablets and confectioned with non-hygroscopic adjuvants and/or in a package with only little or no water vapor permeability.

The method according to the invention for simply and rapidly producing a pharmaceutical preparation of the initially defined kind is essentially characterized in that a carrier of mannitol is loaded or sprayed with a methanolic or alcoholic solution of the active ingredient, whereupon the alcoholic solvent is evaporated until a water factor of below 0.4 and, in particular, below 0.3 has been reached, and tableting is subsequently effected, optionally upon addition of magnesium stearate as a lubricant. By using alcoholic solvents and, in particular, methanolic or ethanolic solvents, of the sodium salts, an accordingly homogenous distribution of the active ingredient on the carrier is ensured. Problems relating to the homogenous distribution of the active ingredient within the tablets ("content uniformity") are, thus, avoidable. After the solvent has been evaporated, an accordingly homogenous distribution of the water-soluble salt on the carrier is ensured, and a stable product will be immediately obtained by verifying the observance of the required water factor. The evaporation of residual moisture along with the drying procedure for evaporating the solvent, i.e. methanol and/or ethanol, for the water-soluble salt of levothyroxin-Na or liothyronin-Na rapidly enables the observance of the desired water factor, whereby, particularly with said methanolic or ethanolic solutions, kind of a drag effect for the removal of excess water is observable during evaporation such that rapid drying will occur.

If additional adjuvants such as, e.g., hygroscopic tablet wetting agents are to be renounced for the tableting procedure, it may be proceeded in a manner that directly tabletable mannitol, particularly Pearlitol, is used as a carrier. When choosing optionally required tableting aids, the use of hygroscopic substances is to be renounced in any event in order to avoid remoisterizing. To this end, it is advantageously proceeded in a manner that hydrophobic adjuvants such as, e.g., magnesium stearate are used as tableting adjuvants and, in particular, lubricants.

In order to ensure, as already mentioned above, that $Ca^{++}$-ions optionally contained in carrier materials do not result in the formation of water-insoluble salts of the hormones, it may be proceeded in a manner that the carrier, prior to being coated or sprayed with the active ingredient solution, is supplemented with EDTA-Na and optionally also citric acid added, in an amount sufficient for complexing bivalent ions of the carrier. The alcoholic active ingredient solution is applied after intermediate drying even at elevated temperatures. Immediately after this, a further amount of aqueous complexing solution is added as described above, in order to bind additionally present ions from solvents or from production apparatus. The respective amount of EDTA-Na used for complexing the $Ca^{++}$-ions in any event is not to be used in excess, since EDTA-Na/citric acid themselves do not readily increase the stability of levothyroxine-Na or liothyronine-Na salts.

Alternatively, the carrier composed of mannitol may optionally be mixed with starch, guar or other granulation aids, loaded with a methanolic or alcoholic solution of the active ingredient and immediately after this moist-granulated with an aqueous solution optionally containing EDTA-Na and/or citric acid. Water is dried off until the desired water activity has been reached, optionally with the assistance of a subsequently added wetting agent. After the admixture of a tableting lubricant, tablets having a low-water-activity are produced. The subsequent preferred package should be water-vapor-impermeable. The thus produced tablets stored at 25° C. are exceptionally stable.

In the following, the invention will be explained in more detail by way of exemplary embodiments and comparative assays.

EXAMPLE 1

The water-soluble salts of the active ingredients were dissolved in an organic, anhydrous solvent such as, e.g., methanol and ethanol. A slight amount of hygroscopic carrier substance in the form of mannitol (Pearlitol 400 DC) was moistened with the active ingredient solution by pouring or spraying. After this, the solvent was removed by fluidized-bed drying or evacuation, with a water factor of 0.3 having been adjusted during the drying procedure. No wetting agent at all was used for tableting. Magnesium stearate was used as a tableting lubricant. The following composition was selected in this exemplary embodiment:

| | |
|---|---:|
| Pearlitol 400 DC | 2749 g |
| Methanol | 60 g |
| Levothyroxine-Na | 1.632 g |
| Magnesium stearate | 32 g |

The thus obtained mixture was directly tabletable without any problem, whereby tablets perfect in terms of appearance, hardness, friability and other pharmaceutical parameters were obtained. The tablet disintegrated within a minute while forming a clear solution except for the Mg stearate floating on the water surface. It is to be anticipated that an optimum bioavailability of the active ingredients is provided, since no other insoluble adjuvants apart from slight amounts of insoluble Mg stearate are present in the dissolution solution.

These tablets had a water factor of 0.2 at a room temperature of 25° C. The water absorption was examined in a test during storage at 25° C., 60% relative humidity and a storage time of 24 hrs against tablets of a conventional formulation (containing e.g. tablet wetting agents as well as other pharmaceutical adjuvants), which had likewise been previously dried to a water factor of 0.2. With the configuration according to the invention no more than 0.11% water absorption and a water factor of 0.3 were observed, while the conventional formulation achieved a water absorption of 0.75% (almost 7 times higher) and a water factor of 0.5.

EXAMPLE 2

Prior to the application of the solution of methanol and levothyroxine-Na as already effected in Example 1, the same amount of Pearlitol, i.e. 2749 g, in Example 2 was previously wetted with 60 g methanol and subsequently pretreated with a solution of 40 g water, 0.12 g anhydrous citric acid and 4.0 g EDTA-disodium. The mixture obtained in this manner was dried to a water factor of 0.2 to 0.25 and subsequently tableted, a good tabletability and tablet disintegration having been observed within a period of approximately 1 minute. The statements made in Example 1 apply also in this case. The active ingredient is homogenously applied on the carrier as in Example 1, and there is no danger of demixing ("content uniformity"). The additional protect against bivalent ions by the applied complexing solution prevents any deactivation of the active ingredient.

EXAMPLE 3

In Example 3, two drying procedures were performed, wherein a first drying procedure took place after the treatment of Pearlitol with the previously described EDTA solution and methanol, whereupon the application of the active ingredient with the previously described methanolic solution was simultaneously effected with another partial amount of the EDTA disodium solution, whereupon a new drying procedure followed.

EXAMPLE 4

This example demonstrates that even in the production by a conventional aqueous granulation method and with the employment of usual tableting adjuvants such as a carrier (mannitol), granulation agent (guar), tablet wetting agent (sodium carboxy-methyl starch) lubricant (magnesium stearate and talc) as well as usual complexing agents (EDTA-Na, citric acid), a tablet exhibiting an exceptional active ingredient stability will be obtained, if the water activity is adjusted according to instructions (0.3) and a tight package is subsequently provided.

In this exemplary embodiment, the following composition was chosen:

| | |
|---|---|
| Mannitol | 11.78944 kg |
| Guar | 0.44 kg |
| Methanol | 0.3 kg |
| Levothyroxine-Na | 0.00816 kg |
| Water | 2.5 kg |
| EDTA-Na | 0.08 kg |
| Citric acid | 0.0024 kg |
| Sodium carboxymethyl starch | 1.2 kg |
| Talc | 0.32 kg |
| Magnesium stearate | 0.16 kg |

The carrier mixed with guar was loaded with the active ingredient solution and subsequently supplemented with an aqueous solution of EDTA-Na plus citric acid and moist-granulated, whereupon drying to a water activity of below 0.3 was effected. Tablets produced with a water activity of 0.45 and stored at 25° C. and 60% RH for 12 months in PVC blisters show an active ingredient content of only 88.6% of the declared value (originally 100%), thus being no longer marketable. The same tablets, dried to a water activity of 0.3 and blistered in PVC, yet packed in water-vapor-tight sachets, when stored under the same conditions, after 12 months show the original content of 99.6% taking into account normal analytical variations. These tablets are, therefore, exceptionally stable.

The following stability improvements have been obtained for the preparations corresponding to examples 1 to 3, said stability improvements having been determined for different active ingredient concentrations:

100 µg levothyroxine-Na, relative humidity 40-50% (water factor 0.4 to 0.5). The portion of levothyroxine-Na dropped to 87% by weight after 3 months, whereby storage conditions at 40° C. and 75% relative humidity were chosen to accelerate results. By contrast, the preparations containing 100 µg levothyroxine-Na at a water factor of 0.3 still showed an activity of 92.9% after 3 months. The same storage conditions and measurements for preparations containing 160 µg levothyroxine-Na at water factors of 0.4 to 0.5 showed 90.7% by weight of residual activity after 3 months, whereas activities of 95.2% by weight of the original quantity were determined at a water factor of 0.3. With combination preparations containing levothyroxine-Na and liothyronine-Na, comparable improvements were observed, whereby, with a preparation containing but 25 µg liothyronine-Na, the content at a water factor of 0.4 to 0.5 had already dropped to 87.2% after 1 month, whereas the respective analysis at a water factor of 0.25 still revealed 97.7% by weight of the employed quantity to be active after one month.

Overall, direct tableting under dry conditions has turned out to constitute a particularly rapid and particularly simple mode of procedure for the production of an accordingly homogenous composition exhibiting long-term stability.

The invention claimed is:

1. A solid pharmaceutical preparation comprising water-soluble salts of levothyroxine as an active ingredient,
   wherein water activity of said pharmaceutical preparation is adjusted to values of below 0.4 and above 0.1, measured at a room temperature of 25° C.

2. The pharmaceutical preparation according to claim 1, wherein the water activity of said pharmaceutical preparation is adjusted to values ranging from 0.1 to 0.3, measured at a room temperature of 25° C.

3. The pharmaceutical preparation according to claim 1, wherein a methanolic or ethanolic solution of said active ingredient is homogenously applied on a carrier.

4. The pharmaceutical preparation according to claim 3, wherein the carrier is a water-soluble carrier.

5. The pharmaceutical preparation according to claim 4, wherein mannitol is used as said water-soluble carrier.

6. The pharmaceutical preparation according to claim 3, wherein the carrier is treated with an amount of EDTA-Na substantially corresponding to a $Ca^{++}$-content of the carrier.

7. The pharmaceutical preparation according to claim 1, wherein the preparation is in the form of tablets and is confectioned with non-hygroscopic adjuvants.

8. The pharmaceutical preparation according to claim 3, wherein said carrier is mixed with starch, guar or granulation aids.

9. The pharmaceutical preparation according to claim 3, wherein the carrier is treated with an amount of EDTA-Na substantially corresponding to a $Ca^{++}$-content of the carrier, and citric acid.

10. The pharmaceutical preparation according to claim 1, wherein the preparation is in the form of tablets and is confectioned in a package with little or no water-vapor permeability.

* * * * *